United States Patent
Beaulieu et al.

(10) Patent No.: US 9,606,242 B2
(45) Date of Patent: Mar. 28, 2017

(54) PLANAR AND VOLUMETRIC DOSIMETER WITH SCINTILLATING MATERIAL FOR RADIOTHERAPY TREATMENT USING TOMOGRAPHIC RECONSTRUCTION

(76) Inventors: Luc Beaulieu, Quebec (CA); Luc Gingras, Quebec (CA); Mathieu Goulet, Quebec (CA); Louis Archambault, Quebec (CA)

( * ) Notice: Subject to any disclaimer, the term of this patent is extended or adjusted under 35 U.S.C. 154(b) by 0 days.

(21) Appl. No.: 14/009,139

(22) PCT Filed: Mar. 29, 2012

(86) PCT No.: PCT/CA2012/000283
§ 371 (c)(1),
(2), (4) Date: Feb. 28, 2014

(87) PCT Pub. No.: WO2012/129661
PCT Pub. Date: Oct. 4, 2012

(65) Prior Publication Data
US 2014/0217295 A1    Aug. 7, 2014

Related U.S. Application Data (60) Provisional application No. 61/470,817, filed on Apr. 1, 2011.

(51) Int. Cl.
*G01T 1/29* (2006.01)
*G01T 1/105* (2006.01)
*G01T 1/02* (2006.01)
*G01T 1/203* (2006.01)
*A61N 5/10* (2006.01)

(52) U.S. Cl.
CPC ............ *G01T 1/105* (2013.01); *A61N 5/1071* (2013.01); *G01T 1/023* (2013.01); *G01T 1/2985* (2013.01); *A61N 2005/1076* (2013.01); *G01T 1/2033* (2013.01)

(58) Field of Classification Search
CPC ........ G01T 1/105; G01T 1/201; A61N 5/1071
See application file for complete search history.

(56) References Cited

U.S. PATENT DOCUMENTS

| | | | | |
|---|---|---|---|---|
| 5,856,673 | A * | 1/1999 | Ikegami | .......... G01T 5/08 250/368 |
| 2002/0131552 | A1* | 9/2002 | Nishizawa et al. | ............. 378/65 |
| 2006/0153341 | A1* | 7/2006 | Guyonnet et al. | ............ 378/207 |

* cited by examiner

*Primary Examiner* — David Porta
*Assistant Examiner* — Shun Lee
(74) *Attorney, Agent, or Firm* — Bereskin & Parr LLP (57) ABSTRACT

According to one aspect, a planar and volumetric dosimeter for use with a radiotherapy machine having a radiation source. The dosimeter includes a scintillating assembly including a plurality of scintillating optical fibers and configured to generate a light output in response to incident dose distribution thereon from the radiation source, and a photodetector operable to convert optical energy emitted by the scintillating assembly to electrical signals for determining actual two-dimensional (2D) or three-dimensional (3D) dose distribution incident on the scintillating assembly using a tomographic reconstruction algorithm.

11 Claims, 11 Drawing Sheets

PLANAR AND VOLUMETRIC DOSIMETER WITH SCINTILLATING MATERIAL FOR RADIOTHERAPY TREATMENT USING TOMOGRAPHIC RECONSTRUCTION

RELATED APPLICATIONS

This application claims the benefit of U.S. Provisional Patent Application Ser. No. 61/470,817 filed Apr. 1, 2012 and entitled PLANAR AND VOLUMETRIC DOSIMETER WITH SCINTILLATING MATERIAL FOR RADIOTHERAPY TREATMENT USING TOMOGRAPHIC RECONSTRUCTION, the entire contents of which are hereby incorporated by reference herein for all purposes.

TECHNICAL FIELD

The embodiments described herein relate to the field of x-ray and particle radiation dosimetry, and in particular to two-dimensional (planar) and three-dimensional (volumetric) dosimetry using tomographic reconstruction algorithms.

INTRODUCTION

Radiation therapy, or "radiotherapy", is the medical use of ionizing radiation, for example to control malignant cells in cancer treatments. Most frequently, radiation therapy makes use of x-ray or particle beams originating from outside a patient's body (i.e. external radiotherapy).

Because of their inherent complexity, some more advanced modes of external beam radiation treatment, such as Intensity Modulated Radiation Therapy (IMRT), helical tomotherapy, radiosurgery and Intensity Modulated Arc Therapy (IMAT), are verified experimentally before the treatment is administered. In particular, the dose distribution may at least be measured in a plurality of positions in space, such as in a two-dimensional plane.

Most often, such dosimetry measurements are performed by an array of periodic detectors. Such detectors can be stacked in a 2D assembly and are usually composed of ionization chambers, semi-conductor diodes (e.g. the Sun Nuclear Mapcheck™), scintillation detectors, or thermoluminescent dosimeters (TLD).

Ionization chamber assemblies are usually limited in spatial resolution because of their significant detector size (usually many millimeters squared). Moreover, the materials used in the fabrication of ionization chambers and diodes (such as silicon and air) are normally not water-equivalent (neither by chemical composition or physical density), and as such their presence in the radiation field tends to perturb the radiation fluence and the resulting dose measurement.

Scintillation detector assemblies on the other hand are usually limited in the number of detectors that can be conveniently stacked in a single array, thus reducing the area of detection or the resolution of the array.

Finally, each TLD normally needs to be read individually after irradiation, which limits the use of a large number of TLDs in a 2D array.

In other cases, direct two-dimensional dose measurement can be conducted by using high resolution radiographic or radiochromic films. However such techniques are subject to several drawbacks. For example, the need to develop radiographic films before they are readable limits their speed and makes their use for online dosimetry generally impractical. Moreover, the development process can affect the film response. Radiographic films are also prone to over-responding to low-energy photons, are not water-equivalent, and their precision is often limited to ±5%.

Radiochromic films on the other hand may be closer to water-equivalence in the energy range used in external beam radiotherapy and do not require developing. However, radiochromic films are temperature dependant and sensitive to ultraviolet light, and achieving better than 5% reproducibility in a routine fashion with radiochromic film tends to be difficult.

Direct two-dimensional dose measurement can also be conducted by a scintillator plate as described for example in U.S. Patent Application Publication Nos. 2004/0178361 (to Fontbonne) and 2009/0218495 (to Leroux et al). However, such methods require extensive correction of the system readings in order to correct for inhomogeneous light dispersion and Čerenkov radiation. Accordingly, the precision of such assemblies tends to be limited, and errors of ±10% on the dose reading are typical.

The above-mentioned detectors allow, at most, measurements in two-dimensional planes. Accordingly, 3D dosimetry with these detectors usually involves summing many 1D or 2D measurements of the dose distribution.

Currently, known detectors that can be used for three-dimensional measurements are dosimetric gels. Dosimetric gels are either based on the behavior of ferrous ions or on the polymerization of a monomer. They can be produced using a large variety of chemical formulas and each has its own set of advantages and disadvantages. However, most gels are made using a delicate fabrication process and require time-consuming development processes that makes them unsuitable for online measurements.

DRAWINGS

The embodiments herein will now be described, by way of example only, with reference to the following drawings, in which:

FIG. 6 is a perspective view of the planar and volumetric dosimeter of FIG. 4a;

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In particular, in some instances, wellknown methods, procedures and components have not been described in detail so as not to obscure the embodiments described herein.

Furthermore, this description is not to be considered as limiting the scope of the embodiments described herein in any way, but rather as merely describing the implementation of various embodiments as described herein. In addition, while certain features have been illustrated and described herein, many modifications, substitutions, changes, and equivalents will now occur to those of ordinary skill in the art. It is therefore to be understood that the appended claims are intended to cover such modifications and changes.

According to one aspect, there is provided a planar and volumetric dosimeter for use with a radiotherapy machine having a radiation source, the planar and volumetric dosimeter comprising a scintillating assembly adapted to generate a light output in response to an incident radiation distribution, and a photo-detector adapted to convert the transmitted optical energy to electrical signals for calculating a two-dimensional (2D) or three-dimensional (3D) incident dose distribution on the scintillating assembly by using tomographic reconstruction algorithms.

The scintillating assembly may include a plurality of scintillating optical fibers, usually in a sizeable length (e.g. at least a few centimeters long), each scintillating optical fiber acting as a weighted dose line integrator. These scintillating optical fibers may be embedded in a phantom medium. The phantom medium may be made of a material with properties relative to radiation that are similar to the material used in the scintillating optical fibers.

In some embodiments, a plurality of collection optical fibers may be coupled to one or both of the opposing ends of the scintillating optical fibers. In such cases one or more photo-detectors may be coupled to the collection optical fibers and be operable to convert optical energy transmitted by the collection optical fibers into electrical signals.

In some embodiments, the scintillation optical fibers of the scintillating assembly may be disposed in one or more imaging planes. These imaging planes may be disposed and oriented following different geometries in the dosimeter volume (e.g. in a series of parallel disks or in a series of concentric cylinders or "rings"). The light intensities collected in one imaging plane may be configured to represent weighted dose line integrals of the incident 2D dose distribution on that imaging plane. By using tomographic reconstruction algorithms on these weighted dose line integrals, the incident 2D dose distribution on the imaging plane may be calculated.

In some embodiments, the 3D dose distribution incident on at least a part of the planar and volumetric dosimeter may be determined by the summation or interpolation (or both) of a plurality of 2D dose distributions obtained by one or more imaging plane(s).

In some embodiments, the scintillating optical fibers may be conditioned with UV light in order to increase their optical attenuation.

In some embodiments, both the scintillating assembly and the photo-detector may be rotatable about a given axis of rotation. This axis of rotation may be parallel to the radiation beam axis, perpendicular (orthogonal) to the radiation beam axis, or in some embodiments generally oriented in any spatial direction.

The scintillating assembly may be made of a water-equivalent material with properties relative to radiation that are equivalent to water.

In some embodiments, the scintillating assembly may be located on a treatment table at or near a height of treatment delivery.

In some examples, the light collected by each end of each scintillating optical fiber may be determined by a summation of the contribution of each element of the dose pattern volume according to the following equations:

$$I_{j,\pm} = C_{j,\pm} \sum_i D_i \cdot F_{j,i} \cdot \kappa_j(u_i) \cdot e^{\lambda_{j,\pm}(u_i)}$$

$$u_i = f(x_i, y_i, z_i)$$

where $I_{j,\pm}$ represents the light collected by a single end (+ or −) of the $j^{th}$ scintillating optical fiber, $D_i$ represents the dose deposited in the $i^{th}$ volume element, $F_{j,i}$ represents the percentage of the $i^{th}$ volume element covered by the $j^{th}$ scintillating optical fiber, $\kappa_j$ represents the scintillation efficiency of the $j^{th}$ scintillating optical fiber (i.e. the number of scintillation photons emitted per unit of deposited dose), $\lambda_j$ accounts for the differential light attenuation along the $j^{th}$ scintillating optical fiber, $C_{j,\pm}$ represent the light losses due to the optical coupling of the $j^{th}$ scintillating optical fiber to the photo-detector, $x_i$, $y_i$ and $z_i$ represent the spatial coordinate of the $i^{th}$ volume element, $u_i$ represents the position on the scintillating optical fiber with respect to the reference point on the fiber and f represents the function relating $u_i$ to the coordinates $x_i$, $y_i$ and $z_i$. The preceding equation can also be written in the following vectorial form:

$$I_{j,\pm} = A_{j,\pm} \cdot \vec{D}$$

where $\vec{D}$ represents the dose distribution in vectorial form and $A_{j,\pm}$ represents the row of the projection matrix associated with the + or − side of the $j^{th}$ scintillating optical fiber.

According to another aspect there is provided a method for determining the weighted dose line integral along a single scintillating optical fiber from the light collected by a single end of the scintillating optical fiber according to the following equations:

$$p_j = B_{j,\pm} \cdot \vec{D} = \frac{I_{j,\pm}}{I_{Norm,j,\pm}} B_{j,\pm} \cdot \vec{D}_{norm}$$

$$B_{j,\pm} \cdot \vec{D} = \frac{A_{j,\pm} \cdot \vec{D}}{C_{j,\pm} \cdot \kappa_j(0) \cdot e^{\lambda_{j,\pm}(0)}} = \sum_i D_i \cdot F_{j,i} \cdot \frac{\kappa(u_i)}{\kappa(0)} \cdot e^{(\lambda_{j,\pm}(u_i) - \lambda_{j,\pm}(0))}$$

where $p_j$ represents the weighted dose line integral for the $j^{th}$ scintillating optical fiber, $I_{j,\pm}$ represents the light collected by a single end (+ or −) of the $j^{th}$ scintillating optical fiber when irradiated by a given dose distribution, $I_{Norm,j,\pm}$ represents the light collected by the same end (+ or −) of the $j^{th}$ scintillating optical fiber when irradiated by a known normalization dose distribution, $\vec{D}_{norm}$ represents the known normalization dose distribution in vectorial form, $\vec{D}$ represents the measured dose distribution in vectorial form, $B_{j,\pm}$ represents the row of the modified projection matrix associated with the + or − side of the $j^{th}$ scintillating optical fiber, $F_{j,i}$ represents the percentage of the $i^{th}$ volume element covered by the $j^{th}$ scintillating optical fiber, $\kappa_j$ represents the scintillation efficiency of the $j^{th}$ scintillating optical fiber (i.e. the number of scintillation photons emitted per unit of deposited dose), $\lambda_j$ accounts for the differential light attenuation along the $j^{th}$ scintillating optical fiber, $u_i$ represents the position on the scintillating optical fiber with respect to the reference point on the fiber and $D_i$ represents the dose deposited in the $i^{th}$ volume element of the measured dose distribution. According to another aspect there is provided a method for determining the weighted dose line integral along a single scintillating optical fiber from the light collected by the two opposed ends of the scintillating optical fiber according to the following equation:

$$p_j = B_j \cdot \vec{D} = \sqrt{\frac{I_{j,+} \cdot I_{j,-}}{I_{Norm,j,+} \cdot I_{Norm,j,-}}} \cdot B_j \cdot \vec{D}_{norm}$$

$$B_j \cdot \vec{D} \cong \sum_i D_i \cdot F_{j,i} \cdot \frac{\kappa_j(u_i)}{\kappa_j(0)}$$

where $p_j$ represents the weighted dose line integral for the $j^{th}$ scintillating optical fiber, $I_{j,\pm}$ represents the light collected by the + or − end of the $j^{th}$ scintillating optical fiber when irradiated by a given dose distribution, $I_{Norm,j,\pm}$ represents the light collected by the + or − end of the $j^{th}$ scintillating optical fiber when irradiated by a known normalization dose distribution, $\vec{D}_{norm}$ represents the known dose distribution in vectorial form, $\vec{D}$ represents the measured dose distribution in vectorial form, $B_j$ represents the row of the modified projection matrix associated with the $j^{th}$ scintillating optical fiber, $F_{j,i}$ represents the percentage of the $i^{th}$ volume element covered by the $j^{th}$ scintillating optical fiber, $\kappa_j$ represents the scintillation efficiency of the $j^{th}$ scintillating optical fiber (i.e. the number of scintillation photons emitted per unit of deposited dose), $\lambda_j$ accounts for the differential light attenuation along the $j^{th}$ scintillating optical fiber, $u_i$ represents the position on the scintillating optical fiber with respect to the reference point on the fiber and $D_i$ represents the dose deposited in the $i^{th}$ volume element of the measured dose distribution.

According to another aspect there is provided a method for determining the incident 2D dose distribution incident on an imaging plane composed of a plurality of scintillating fibers for use on a radiotherapy machine having a radiation source, the method comprising using iterative reconstruction techniques on the measured weighted dose line integrals (such as an algebraic reconstruction algorithm or an expectation-maximization algorithm) in conjunction with a total variation (TV) minimization of the resultant dose pattern, the total variation (TV) of the 2D dose distribution being defined as:

$$TV = \sum_i \sqrt{(D_i - D_{i-1})^2 + (D_i - D_{i-m})^2}$$

where $D_i$ represents the dose measured in the $i^{th}$ volume element and m is the number of such volume elements in each row of the 2D dose distribution.

According to another aspect there is provided a method for determining the incident 2D dose distribution on an imaging plane composed of a plurality of scintillating fibers for use on a radiotherapy machine having a radiation source, the method comprising using linear programming algorithms to determine the 2D dose distribution under the constraints that the measured weighted dose line integrals should be respected and that the reconstructed dose distribution should be physically possible and noiseless.

According to some embodiments, a planar and volumetric dosimeter as described herein includes a scintillating assembly and a photo-detector configured to determine the 2D or 3D dose distribution incident on the scintillating assembly. Generally, the scintillating assembly is situated under the primary beam of a medical linear accelerator (also known as a "linac") operable to generate x-rays or particle beams.

In some embodiments, the scintillating assembly includes a plurality of scintillating optical fibers assembled in a phantom volume (i.e. a non-scintillating material).

In some embodiments, the scintillating optical fibers may have a length of a few centimeters or more.

In some embodiments, the scintillating optical fibers are conditioned using UV light in order to increase their optical attenuation.

In some embodiments, the phantom volume is made of plastic or other material that is equivalent to the composition of the scintillating optical fibers.

In some embodiments, the phantom volume is made of a material with at least some properties relative to radiation that are equivalent to water (e.g. a water-equivalent phantom material).

In some embodiments, the scintillating optical fibers of the scintillating assembly are grouped in imaging planes in which a plurality of scintillating optical fibers are aligned parallel to each other in a single planar region within the dosimeter volume. The light intensities collected by all scintillating optical fibers in a given imaging plane are configured to represent weighted dose line integrals of the 2D dose distribution generated in that imaging plane.

In some embodiments, the imaging plane(s) may rotate around an axis of rotation that is perpendicular or normal to the plane(s), obtaining a plurality of weighted dose line integrals of the 2D dose distribution generated in the imaging plane at different angles between the scintillating optical fibers and the dose distribution. Accordingly, by using tomographic reconstruction algorithms on the acquired weighted dose line integrals of the 2D dose distribution, the 2D dose distribution incident on the imaging plane can be determined.

Furthermore, by summing a plurality of such imaging planes, or by translating one or more imaging planes in the dosimeter area, one can obtain a plurality of 2D dose distributions incident on the imaging plane simultaneously. By summing and/or interpolating these 2D dose distributions, one can calculate the 3D dose distribution incident on at least a part of the dosimeter volume.

In some embodiments, the scintillating optical fibers may be grouped in circular imaging planes or "rings", in which a plurality of scintillating optical fibers are grouped in a single cylindrical region or ring in the scintillating assembly. Each scintillating optical fiber may be oriented in the circular imaging plane following a distinct angle in the circular imaging plane. For example, the angle of a particular scintillating optical fiber in the circular imaging plane may be distinct from the angles of the other scintillating optical fibers in the same circular imaging plane.

In some embodiments, the circular imaging planes may be adapted to rotate around their central axis of symmetry. The sum of the weighted dose line integrals of a single scintillating optical fiber after a complete rotation (i.e. 360 degrees) or at least a portion of a complete rotation (i.e. 180 degrees) of the circular imaging plane around its central axis of symmetry may represent a line (1D) projection of the 2D dose distribution generated in the circular imaging plane at an angle defined by the orientation of the scintillating optical fiber in the circular imaging plane. By using tomographic reconstruction algorithms on the acquired weighted dose line integrals of the 2D dose distribution, the 2D dose distribution incident on the circular imaging plane can be determined. Furthermore, by summing a plurality of such circular imaging planes, one can obtain a plurality of 2D dose distributions incident on the imaging plane simultaneously. By summing and interpolating these 2D dose distributions, one can calculate the 3D dose distribution incident on at least a part of the dosimeter volume.

Also generally described herein is a theoretical model for predicting the optical energy produced by scintillating optical fibers and collected at each end thereof as a function of the measured dose distribution.

Also generally described herein are methods of determining the weighted dose line integral along scintillating optical fibers as a function of the optical energy produced by scintillating optical fibers and collected at each end thereof.

Also generally described herein are methods of determining the incident 2D dose distribution on an imaging plane of the planar and volumetric dosimeter. A first determination method uses algebraic reconstruction techniques on the calculated weighted dose line integrals and a total variation (TV) minimization of the resultant dose pattern. A second determination method uses linear programming optimization of the calculated weighted dose line integrals in parallel with physical assumptions on the 2D dose distribution geometry.

Figure 1A:
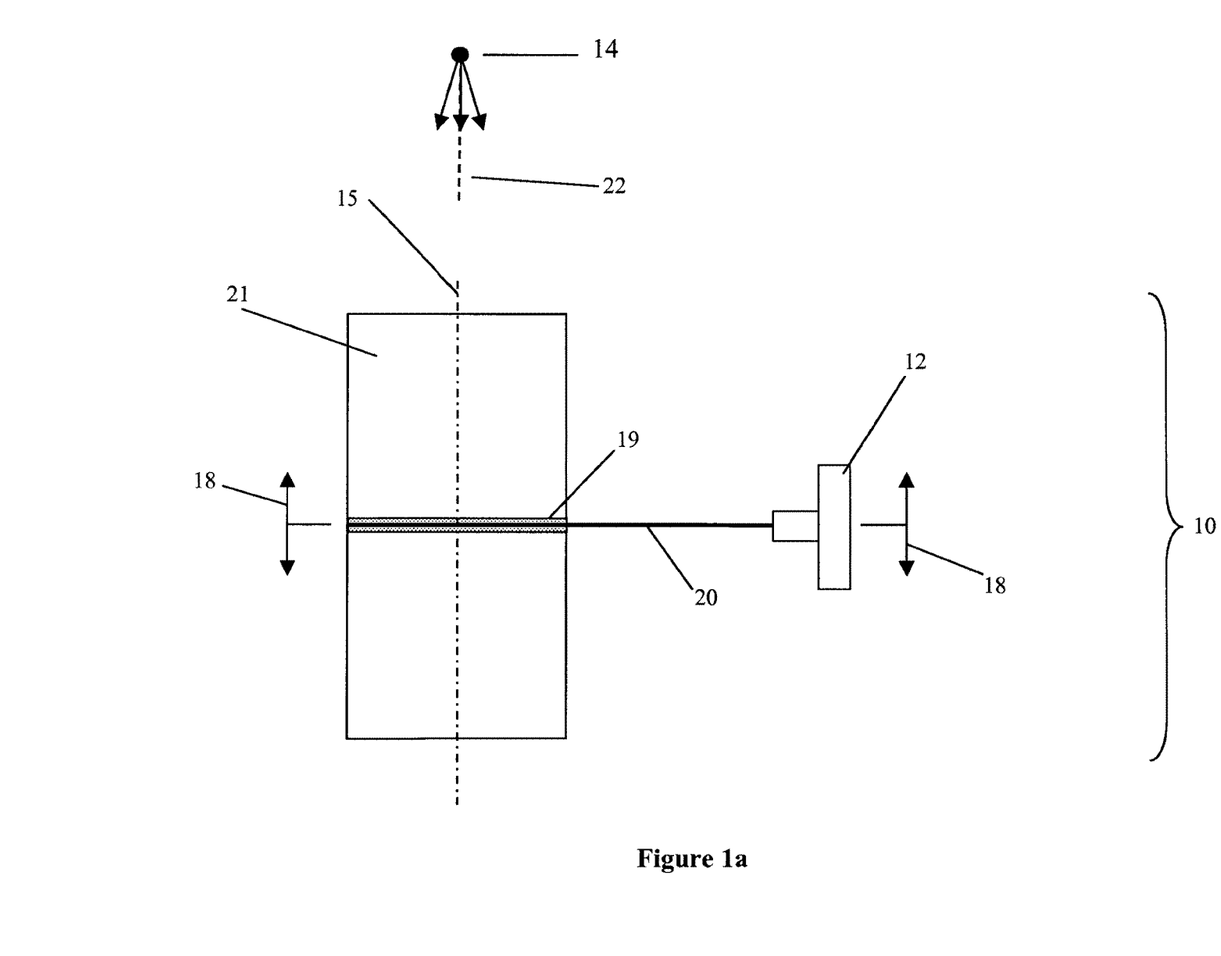
FIGS. 1a and 1b are two schematic side views of a planar and volumetric dosimeter according to some embodiments.

Turning now to FIG. 1a, illustrated therein is a schematic side view of a planar and volumetric dosimeter 10 according to one embodiment. As shown, the planar and volumetric dosimeter 10 includes a scintillating assembly with at least one imaging plane (indicated generally as 19), a plurality of collection optical fibers (indicated generally as 20), a volume of phantom material 21 (e.g. which may be cylindrical as in this exemplary embodiment) and one or more photo-detectors 12 (e.g. a CCD camera or any other suitable photo-detector).

The phantom material 21 and the imaging plane 19 are positioned under the radiation source (indicated schematically as 14) so that the axis of rotation 15 of the planar and volumetric dosimeter 10 is generally aligned with or parallel to the radiation beam axis 22.

In some embodiments, at least one of the imaging plane 19, the collection optical fibers 20 and the photo-detector 12 can undergo a vertical translation 18 (e.g. generally along a direction aligned with the radiation beam axis 22) while the phantom material 21 remains static (i.e. is held in place).

Figure 1B:
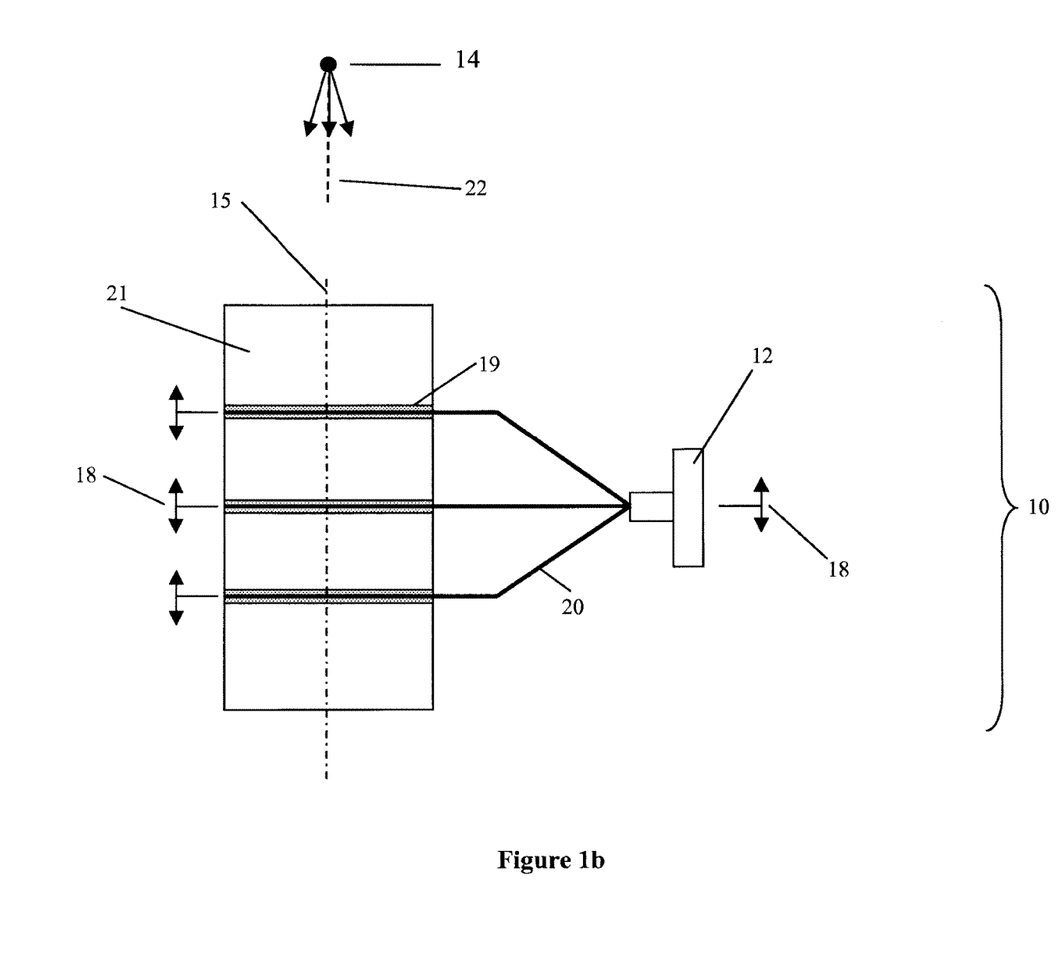

FIG. 1b shows the planar and volumetric dosimeter 10 of FIG. 1a, in which three imaging planes 19 are used. In other embodiments, two imaging planes 19 or more than three imaging planes 19 may be used.

Figure 2:
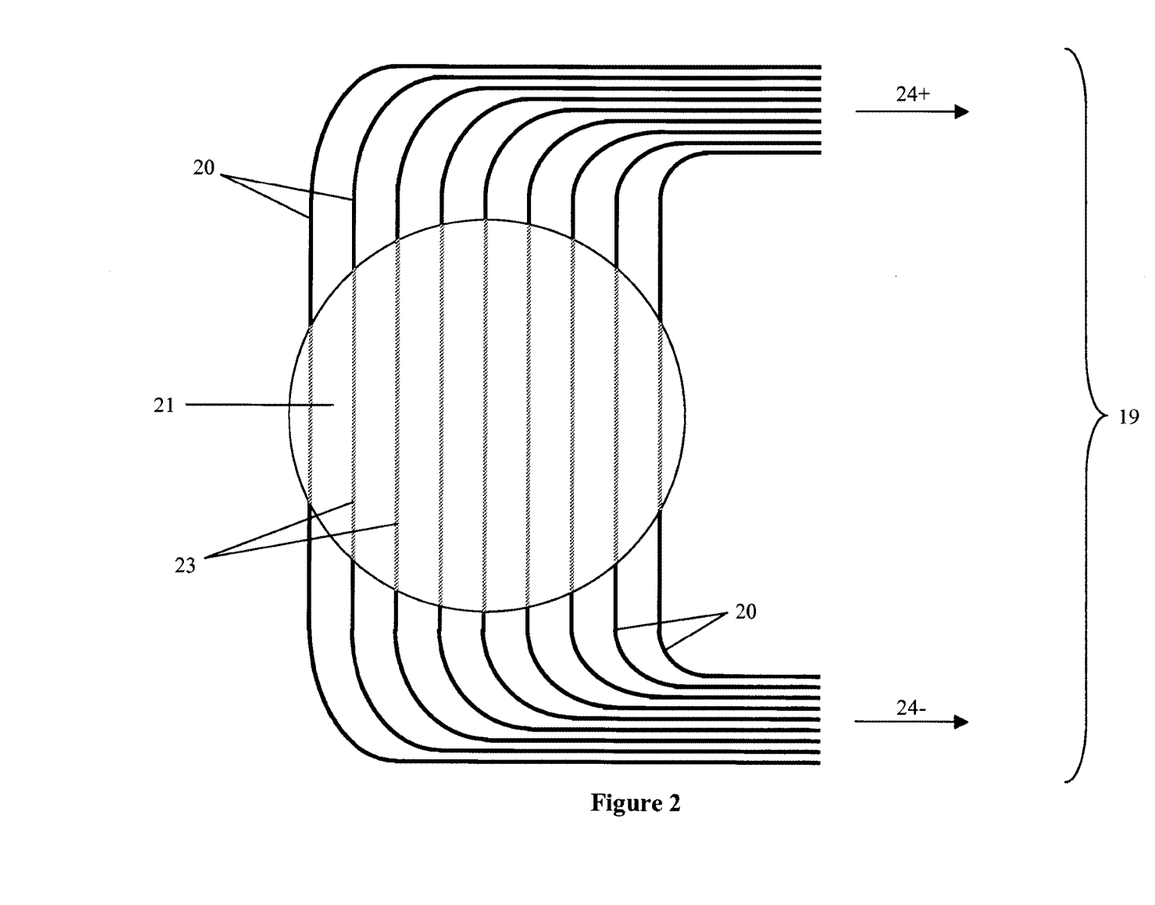
FIG. 2 is a schematic top view representation of a scintillating optical fiber imaging plane as shown in FIGS. 1a and 1b.

FIG. 2 illustrates a schematic top view of an imaging plane 19 from FIGS. 1a and 1b. As shown, the imaging plane 19 includes a plurality of scintillating fibers 23 embedded in the phantom slab 21. Collection optical fibers 20 (e.g. clear or non-scintillating fibers) are coupled to one or more ends of the scintillating fibers 23 so that the light fluxes 24+ and 24− emitted from the ends of the scintillating fibers 23 can be collected by the photo-detector 12 and converted into electrical signals therein.

In some embodiments, the light fluxes 24+ and 24− emitted by the scintillating fibers 23 in the imaging plane 19 and converted to electrical signals by the photo-detector 12 are configured to represent weighted dose line integrals of the 2D dose distribution incident on the imaging plane 19.

Figure 3:
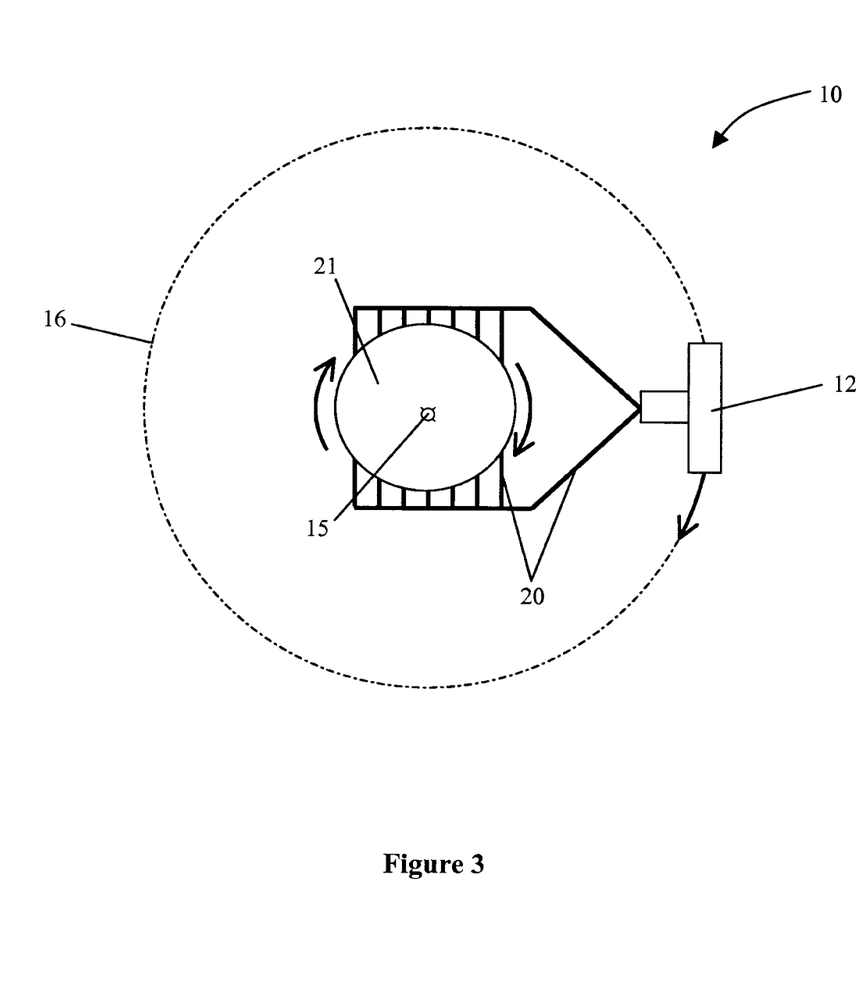
FIG. 3 is a schematic top view of the planar and volumetric dosimeter of FIG. 1a or 1b, viewed from the perspective of the radiation source.

FIG. 3 shows another top view of the planar and volumetric dosimeter 10 of FIG. 1a or 1b, as viewed from the radiation source 14. As shown, the photo-detector 12, the phantom material 21, the imaging plane 19, and the collection optical fibers 20 may all be adapted to rotate together about a central axis of rotation 15. By performing such a rotation, the photo-detector 12 follows a circular trajectory 16 or orbit about the central axis of rotation 15.

When moving along this circular trajectory 16, each imaging plane 19 is able to take a plurality of weighted dose line integrals of the 2D dose distribution incident on the imaging plane 19 at different orientations between the scintillating fibers 23 and the deposited dose distribution. By using tomographic reconstruction algorithms on this plurality of weighted dose line integrals, the 2D dose distribution incident on the imaging plane 19 can be determined.

Furthermore, by applying a vertical translation 18 to each of the imaging planes 19 in addition to the rotation of the planar and volumetric dosimeter 10 around the axis of rotation 15, a plurality of 2D dose distributions at different depths in the phantom material 21 can be acquired simultaneously. By summing or interpolating (or both) between the obtained 2D dose distributions at different depths in the phantom material 21, the 3D dose distribution incident on at least a part of the planar and volumetric dosimeter 10 can be determined.

Figure 4A:
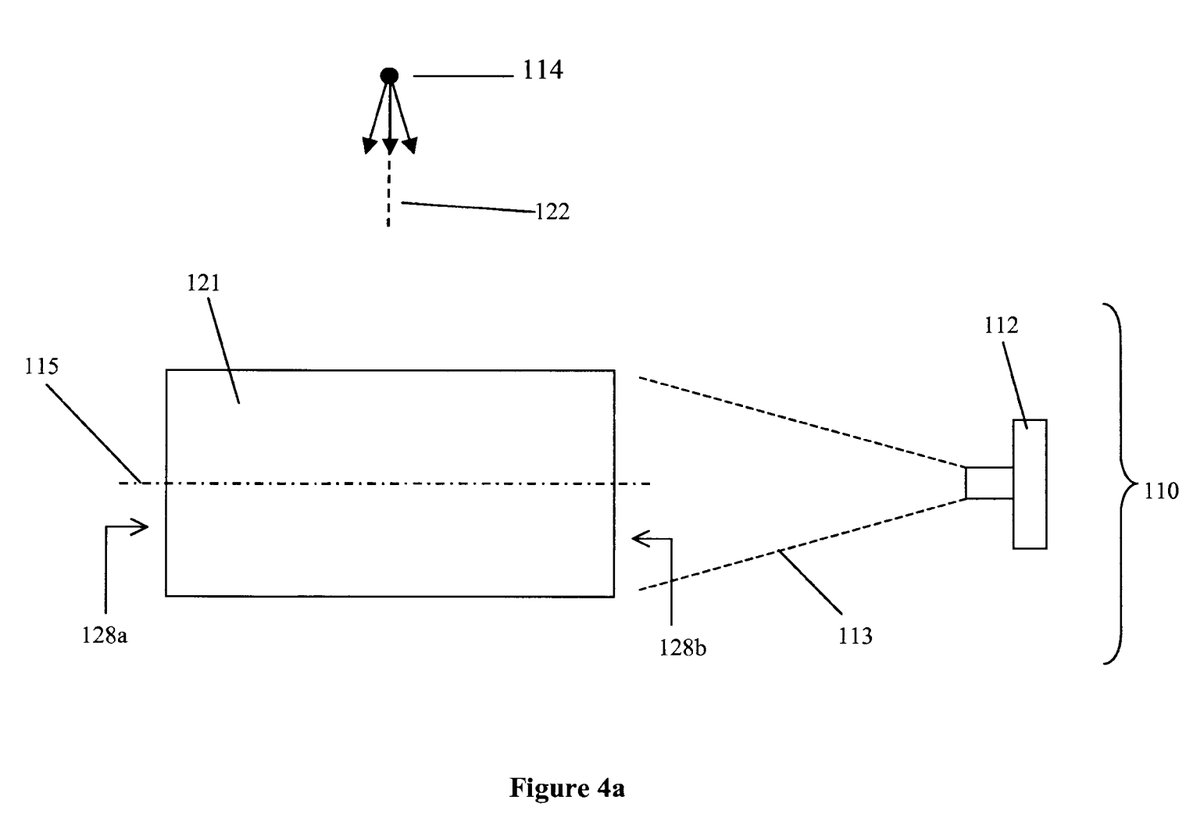
FIGS. 4a and 4b are two schematic side views of a planar and volumetric dosimeter according to some other embodiments.

Turning now to FIG. 4a, illustrated therein is another embodiment of the planar and volumetric dosimeter 110. The planar and volumetric dosimeter 110 may be generally similar to the dosimeter 10 as described above, and where appropriate like elements have been given similar numbers incremented by 100.

As shown, the planar and volumetric dosimeter 110 includes a scintillating assembly composed of a plurality of circular imaging planes 125 (as shown on FIG. 5), a volume of phantom material 121 (cylindrical in this exemplary embodiment) and a photo-detector 112 capable of taking 2D images. The field of view 113 of the photo-detector 112 is generally large enough so that the entire face 128b of the phantom material 121 may be imaged or captured at the same time. The volume of phantom material 121 and the circular imaging planes 125 are positioned under a radiation source (indicated schematically as 114) so that the axis of rotation 115 of the planar and volumetric dosimeter 110 is perpendicular or orthogonal to the radiation beam axis 122. Moreover, the circular imaging planes 125, the phantom material 121 and the photo-detector 112 are all adapted to rotate together about a central axis of rotation 115 that is perpendicular or orthogonal to the radiation beam axis 122.

Figure 4B:
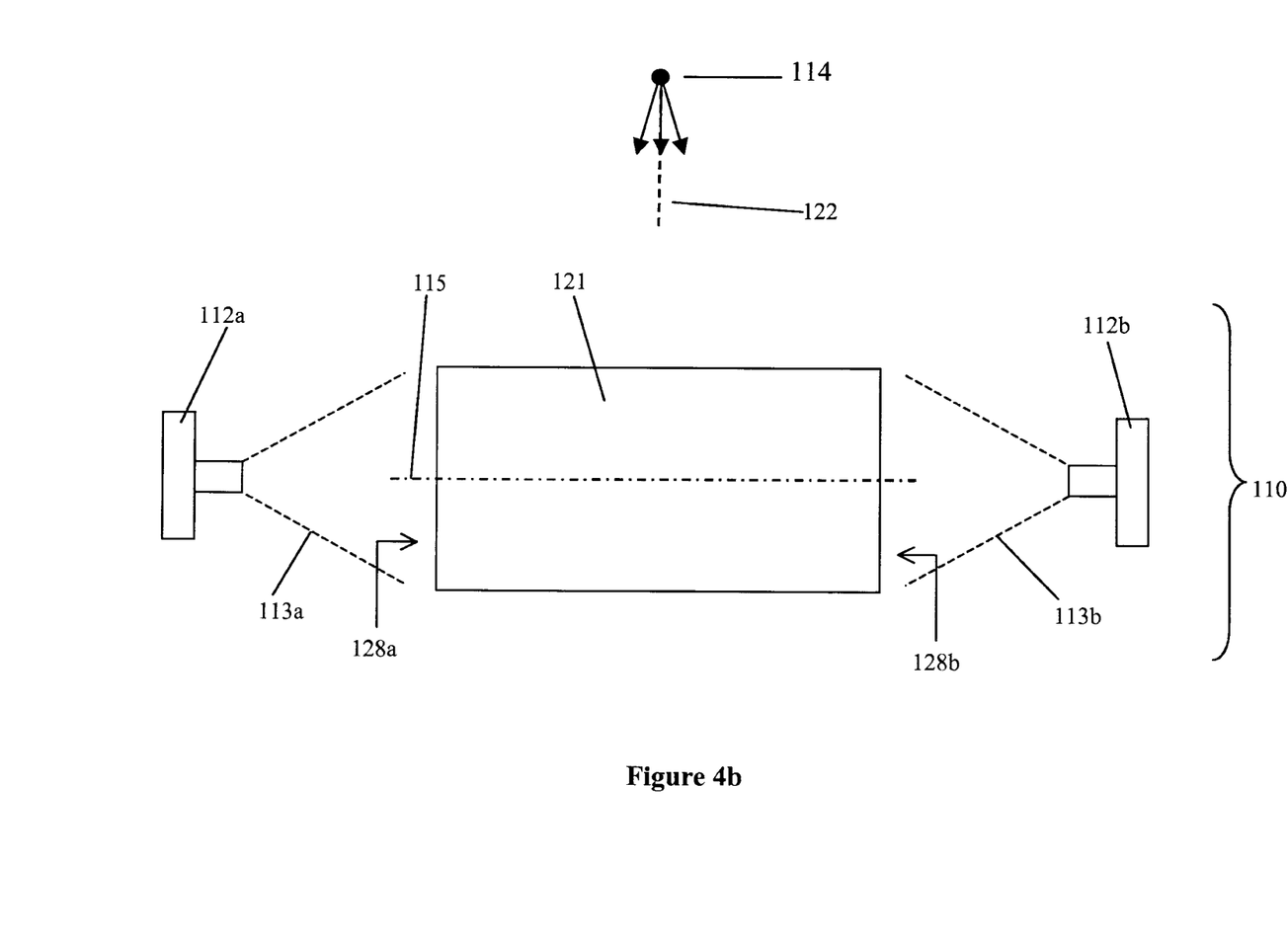

FIG. 4b shows the planar and volumetric dosimeter 110 of FIG. 4a, in which two photo-detectors 112a and 112b capable of taking 2D images are provided. Generally, the two fields of view 113a and 113b of both photo-detectors 112a and 112b are large enough so that both ends or faces 128a and 128b of the phantom material 121 may be imaged at the same time, with the first face 128a being imaged by the first photo-detector 112a and the second face 128b being imaged by the second photo-detector 112b. Generally, the imaging planes 125, the phantom material 121 and the photo-detectors 112a and 112b may be rotated together following a central axis of rotation 115 that is orthogonal to the radiation beam axis 122.

Figure 5:
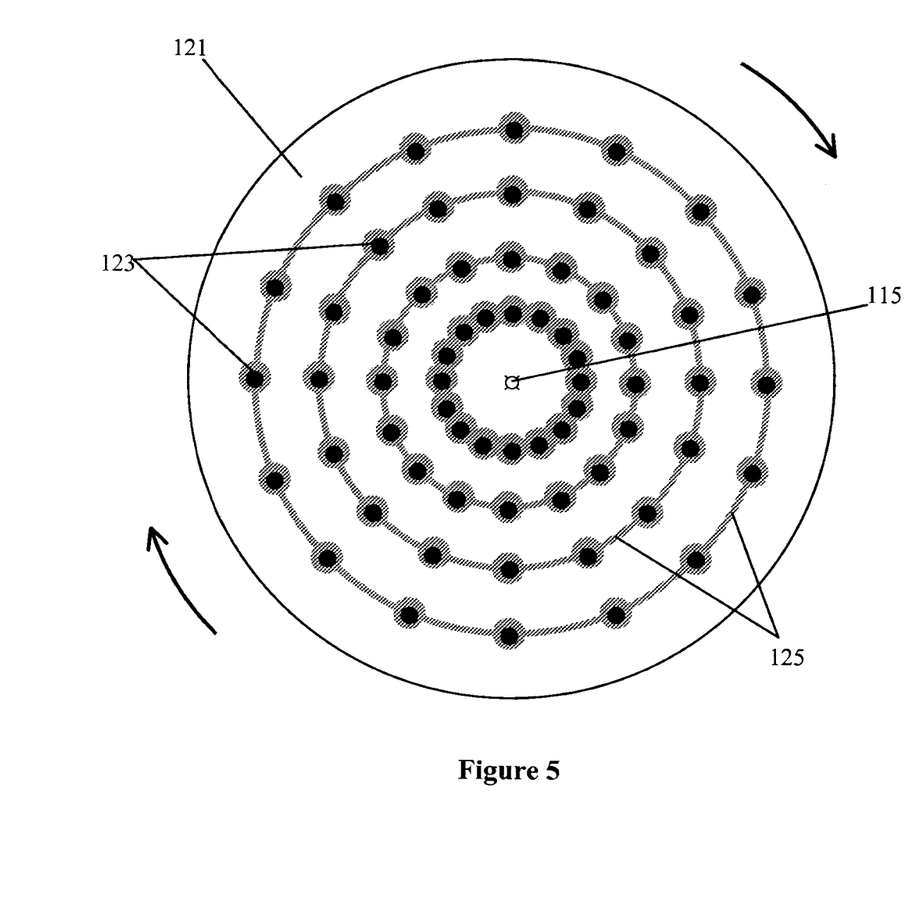
FIG. 5 is a schematic end view of the planar and volumetric dosimeter of FIGS. 4a and 4b, viewed from the perspective of the photo-detector.

FIG. 5 shows the planar and volumetric dosimeter 110 of FIGS. 4a and 4b, as viewed from one of the photo-detectors 112 (e.g. one of the two photo-detectors 112a and 112b). As shown, a plurality of circular imaging planes 125 or rings are provided, which are generally concentric to the central axis of rotation 115. Each imaging plane 125 generally includes a plurality of scintillating optical fibers 123 as illustrated on FIGS. 7a and 7b for example.

Figure 6:
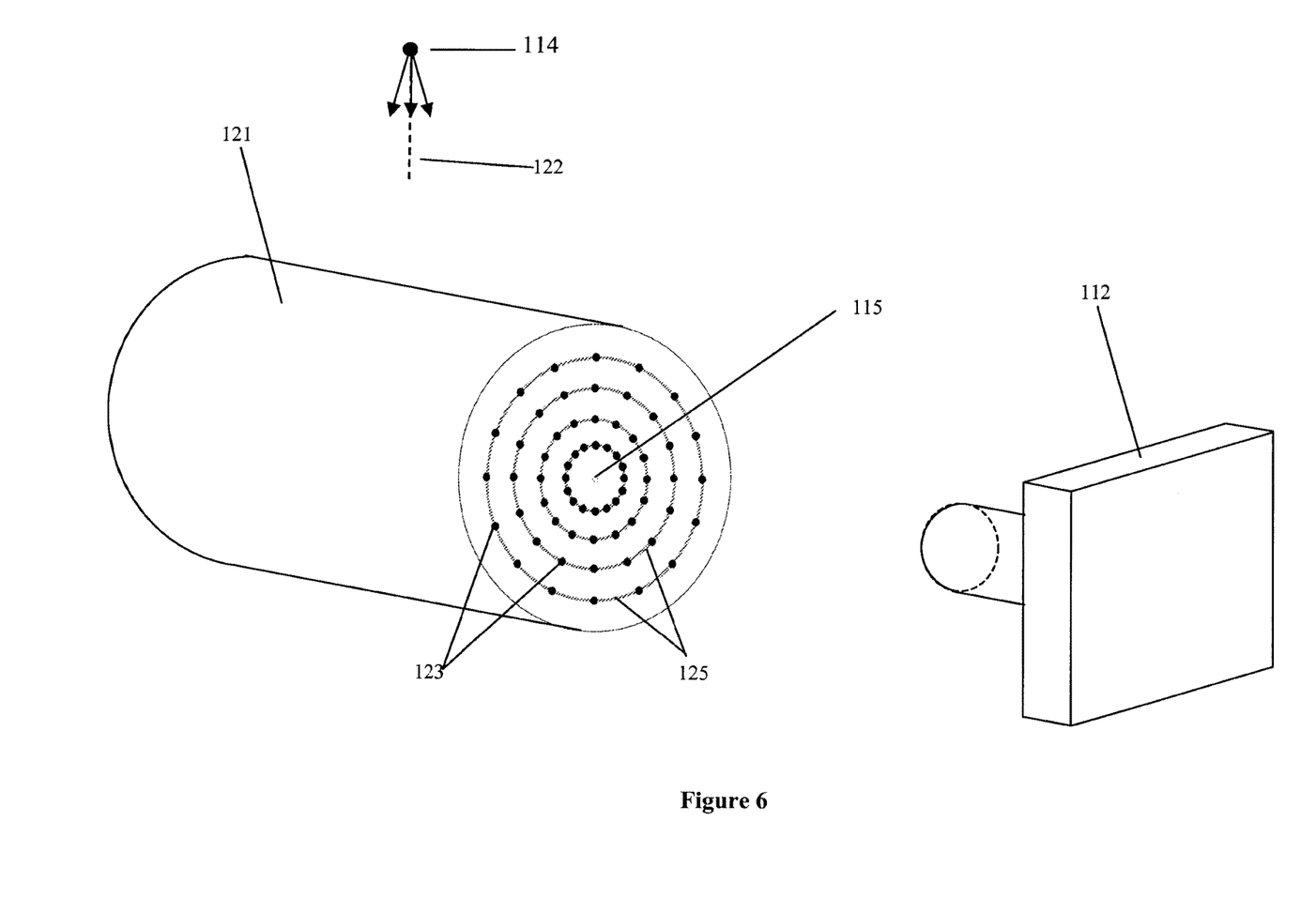

Each scintillating optical fiber 123 may have one end exposed to the photo-detector 112, or both ends exposed to the photo-detectors 112a and 112b. The circular imaging planes 125, the phantom material 121 and the photo-detector(s) 112 can all rotate together about a central axis of rotation 115. For clarity, a perspective view of the planar and volumetric dosimeter 10 is shown in FIG. 6.

Figure 7A:
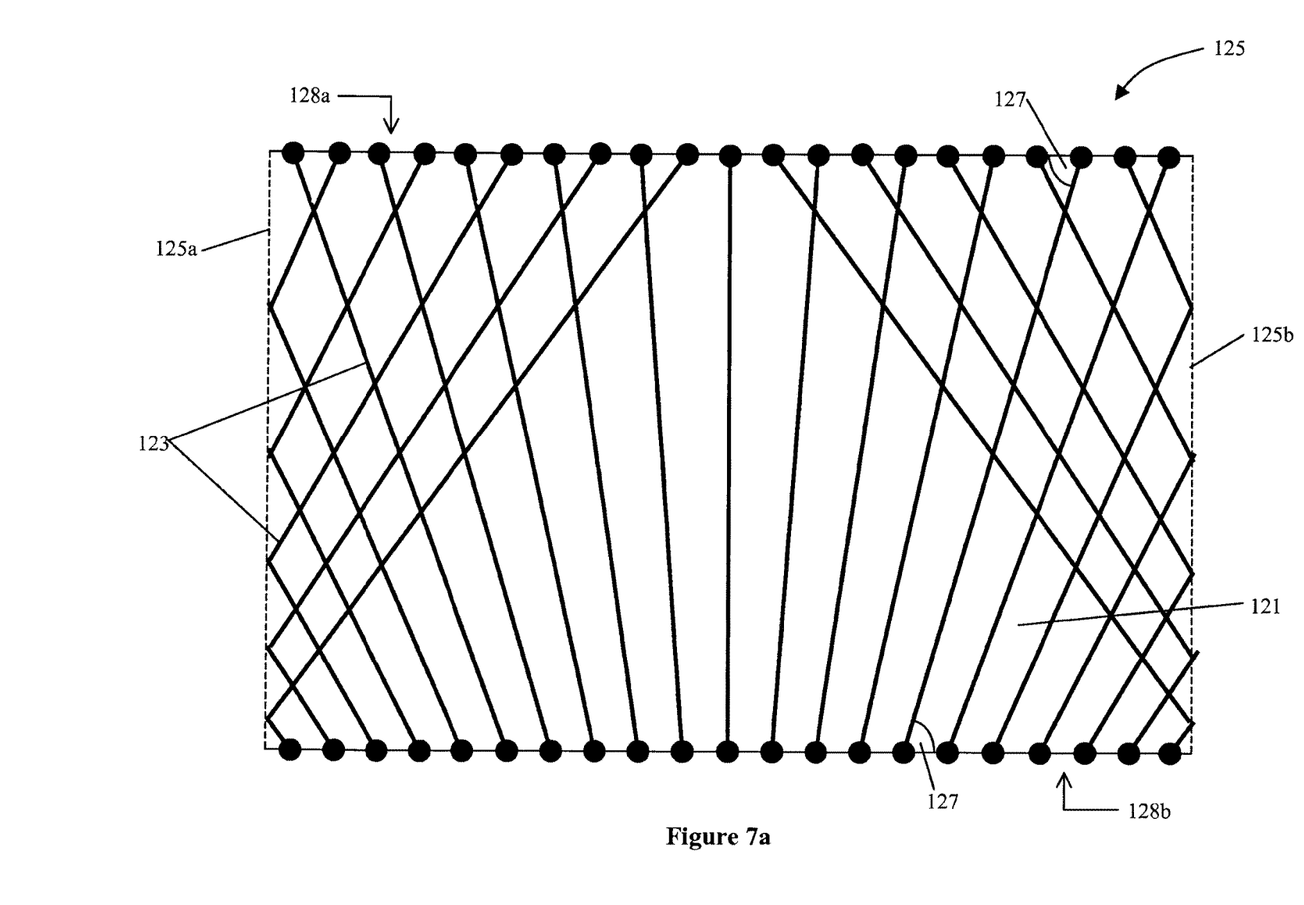
FIGS. 7a and 7b are two schematic views of a circular scintillating optical fiber imaging plane present in FIG. 5.

FIG. 7a illustrates a planar representation of a circular imaging plane 125 shown in FIG. 5. It will be understood that the right and left extremities 125a, 125b of FIG. 7a are in fact coincident, and that the circular plane 125 is of a cylindrical form.

As shown, the circular imaging plane 125 includes the plurality of scintillating optical fibers 123, with each scintillating fiber 123 inclined at a different angle 127 with respect to the faces 128a and 128b of the phantom material 121. Thus, after a complete rotation (e.g. 360 degrees) of the planar and volumetric dosimeter 110 around its central axis of rotation 115, the sum of all the light fluxes emitted by a single scintillating optical fiber 123 and converted to a weighted dose line integral by the photo-detector(s) 112 represents a line (1D) projection of the 2D dose distribution incident on the circular imaging plane 125 in which the scintillating optical fiber belongs.

With a plurality of line (1D) projections obtained from the plurality of scintillating optical fibers 123 and using tomographic reconstruction algorithms, the 2D dose distribution incident on each circular imaging plane 125 may be determined. Furthermore, by using a plurality of circular imaging planes 125, a plurality of 2D dose distributions at different radius from the central axis of rotation 115 can be acquired simultaneously. By summing or interpolating (or both) between the obtained 2D dose distributions at different radii in the phantom material 121, the 3D dose distribution incident on at least a part of the planar and volumetric dosimeter 110 can be determined.

Figure 7B:
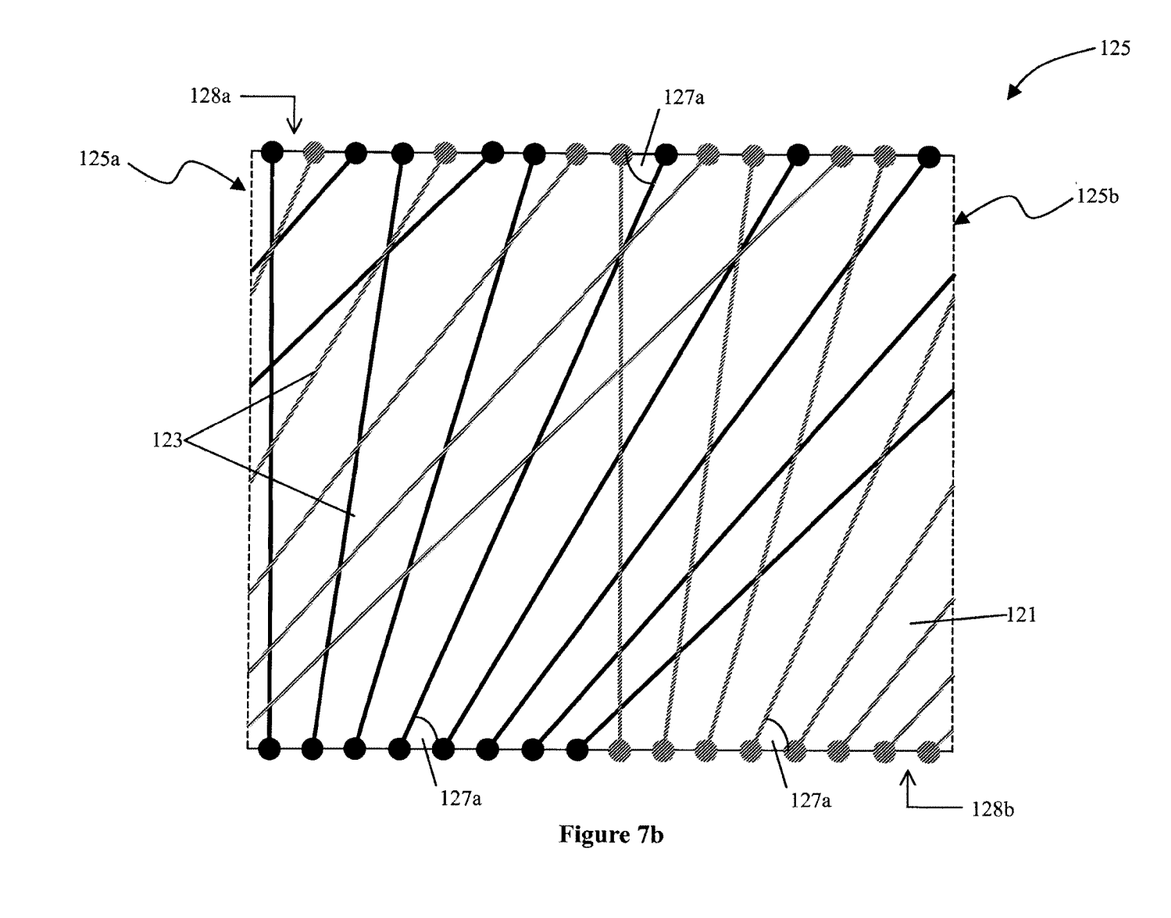

Turning now to FIG. 7b, in some embodiments each of the scintillating fibers 123 need not have a different or unique angle with respect to the faces 128a and 128b of the phantom material 121. For example, as shown in this particular embodiment, at least two scintillating optical fibers 123 may share the same unique angle 127a, and could for example be separated by half of the circumference of the circular imaging plane 125.

By using such a layout of scintillating optical fibers 123 in the circular imaging plane 125, only half a rotation (e.g. 180 degrees) of the dosimeter 110 around its central axis of rotation 115 may be required to obtain 1D projections (e.g. line projections) of the 2D dose distribution incident on the circular imaging plane 125, for a total of one 1D projection per pair of scintillating optical fibers sharing the same unique angle 127a.

Figure 8:
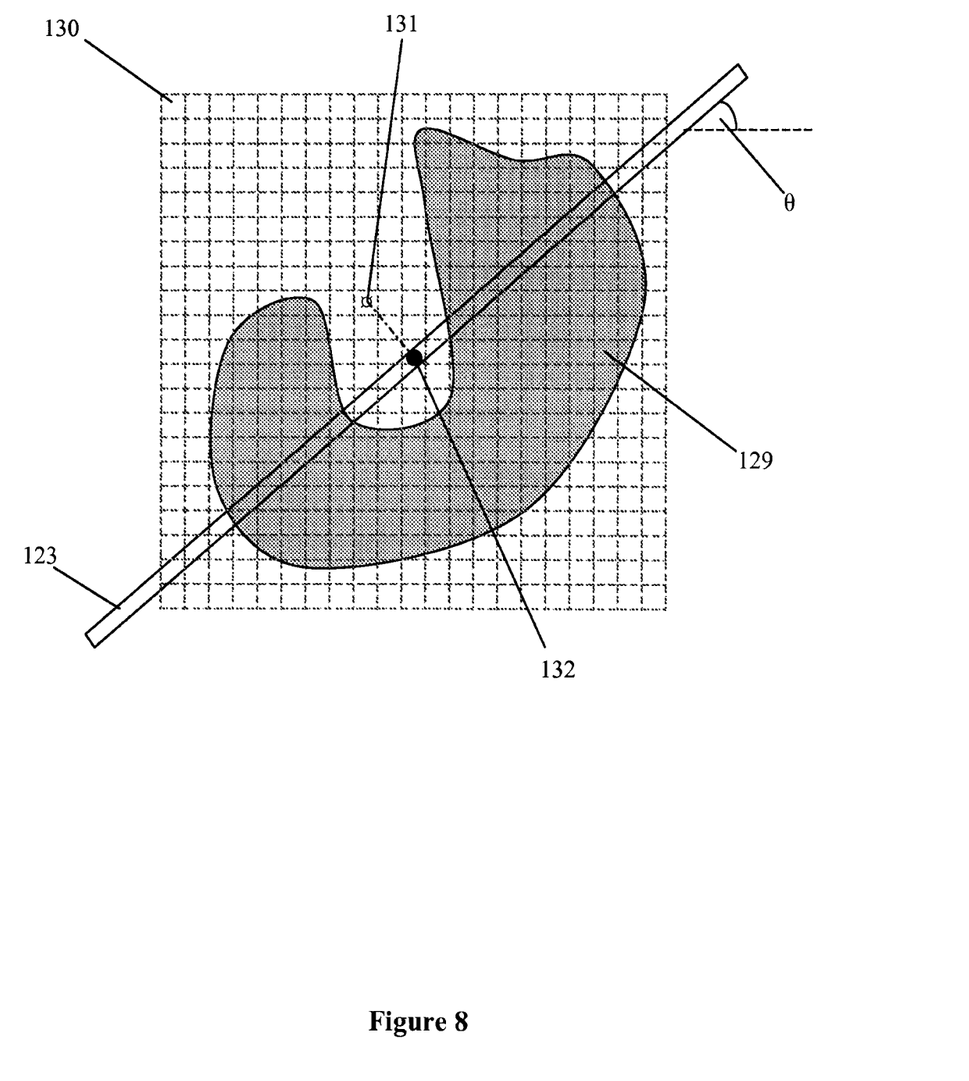
FIG. 8 is schematic top view of a dose deposition pattern and a scintillating fiber according to some embodiments.

Also described herein is a model that predicts the optical energy produced by scintillating optical fibers (e.g. scintillating optical fibers 123) when irradiated by a given dose distribution 129. From this model and following the deposition of a dose distribution 129, as shown in FIG. 8, the light emitted by each end (+/−) of the j$^{th}$ scintillating optical fiber 123 (i.e. $I_{j+}$ and $I_{j-}$) is determined by the summation of the contribution of each volume element 130:

$$I_{j,\pm} = C_{j,\pm} \sum_i D_i \cdot F_{j,i} \cdot \kappa_j(u_i) \cdot e^{\lambda_{j,\pm}(u_i)} \quad (1)$$

$$u_i = f(x_i, y_i, z_i) \quad (2)$$

where $D_i$ represents the dose deposited in the i$^{th}$ volume element 130, $F_{j,i}$ represents the percentage of the i$^{th}$ volume element 130 covered by the j$^{th}$ scintillating optical fiber 123, $\kappa_j$ represents the scintillation efficiency of the j$^{th}$ scintillating optical fiber 123 (i.e. the number of scintillation photons emitted per unit of deposited dose), $\lambda_j$ accounts for the differential light attenuation along the scintillating optical fiber 123, $C_{j,\pm}$ represent the light losses due to the optical coupling of the j$^{th}$ scintillating optical fiber 123 to the photo-detector, $x_i$, $y_i$ and $z_i$ represent the spatial coordinate of the i$^{th}$ volume element 130, $u_i$ represents the position on the scintillating optical fiber 123 with respect to a reference point on the fiber 132 (e.g. the position on the scintillating optical fiber 123 closest to the axis of rotation 131) and f represents the function relating $u_i$ to the coordinates $x_i$, $y_i$ and $z_i$. In some embodiments, this reference point on the fiber 132 can be defined as the center of the scintillating optical fiber 123. Equation 1 can also be written in the following vectorial form:

$$I_{j,\pm} = A_{j,\pm} \cdot \vec{D} \quad (1a)$$

where $\vec{D}$ represents the dose distribution 129 in vectorial form and $A_{j,\pm}$ represents the row of the projection matrix associated with the + or − side of the j$^{th}$ scintillating optical fiber 123. It will be understood that the representation in FIG. 8 is limited to two spatial dimensions for clarity only and that the preceding analysis can easily be extended in the three spatial dimensions.

One method for calibrating a planar and volumetric dosimeter is described in U.S. Provisional Patent Application No. 61/375,125 filed on Aug. 19, 2010 (now U.S. Non-Provisional application Ser. No. 13/207,624) entitled FLUENCE MONITORING DEVICES WITH SCINTILLATING FIBERS FOR X-RAY RADIOTHERAPY TREATMENT AND METHODS FOR CALIBRATION AND VALIDATION OF SAME, the entire contents of which are hereby incorporated herein by reference for all purposes.

Also described herein is a method for determining the weighted dose line integral along a single scintillating optical fiber from the light collected by a single end of the scintillating optical fiber according to the following equation:

$$p_j = B_{j,\pm} \cdot \vec{D} = \frac{I_{j,\pm}}{I_{Norm,j,\pm}} B_{j,\pm} \cdot \vec{D}_{norm} \quad (3)$$

$$B_{j,\pm} \cdot \vec{D} = \frac{A_{j,\pm} \cdot \vec{D}}{C_{j,\pm} \cdot \kappa_j(0) \cdot e^{\lambda_{j,\pm}(0)}} = \sum_i D_i \cdot F_{j,i} \cdot \frac{\kappa(u_i)}{\kappa(0)} \cdot e^{(\lambda_{j,\pm}(u_i) - \lambda_{j,\pm}(0))} \quad (3a)$$

where $p_j$ represents the weighted dose line integral for the j$^{th}$ scintillating optical fiber, $I_{j,\pm}$ represents the light collected by a single end (+ or −) of the j$^{th}$ scintillating optical fiber when irradiated by a given dose distribution, $I_{Norm,j,\pm}$ represents the light collected by the same end (+ or −) of the j$^{th}$ scintillating optical fiber when irradiated by a known normalization dose distribution, $\vec{D}_{norm}$ represents the known dose distribution in vectorial form, $\vec{D}$ represents the measured dose distribution in vectorial form, $B_{j,\pm}$ represents the row of the modified projection matrix associated with the + or − side of the $j^{th}$ scintillating optical fiber, represents the percentage of the $i^{th}$ volume element covered by the $j^{th}$ scintillating optical fiber, $\kappa_j$ represents the scintillation efficiency of the $j^{th}$ scintillating optical fiber (i.e. the number of scintillation photons emitted per unit of deposited dose), $\lambda_j$ accounts for the differential light attenuation along the $j^{th}$ scintillating optical fiber, $u_i$ represents the position on the scintillating optical fiber with respect to the reference point on the fiber and $D_i$ represents the dose deposited in the $i^{th}$ volume element of the measured dose distribution. It will be understood that the projection calculated using equation (3) and (3a) will normally be dependant on the light attenuation in the scintillating optical fiber, so that $p_j$ will be different if calculated from the + or the − side of the scintillating optical fiber.

Also described herein is a method for determining the weighted dose line integral along a single scintillating optical fiber from the light collected by the two opposed ends of the scintillating optical fiber according to the following equation:

$$p_j = B_j \cdot \vec{D} = \sqrt{\frac{I_{j,+} \cdot I_{j,-}}{I_{Norm,j,+} \cdot I_{Norm,j,-}}} \cdot B_j \cdot \vec{D}_{norm} \quad (4)$$

$$B_j \cdot \vec{D} \cong \sum_i D_i \cdot F_{j,i} \cdot \frac{\kappa(u_i)}{\kappa(0)} \quad (4a)$$

where $p_j$ represents the weighted dose line integral for the $j^{th}$ scintillating optical fiber, $I_{j,\pm}$ represents the light collected by the + or − end of the $j^{th}$ scintillating optical fiber when irradiated by a given dose distribution, $I_{Norm,j,\pm}$ represents the light collected by the + or − end of the $j^{th}$ scintillating optical fiber when irradiated by a known normalization dose distribution, $\vec{D}_{norm}$ represents the known dose distribution in vectorial form, $\vec{D}$ represents the measured dose distribution in vectorial form, $B_{j,\pm}$ represents the row of the modified projection matrix associated with the + or − side of the $j^{th}$ scintillating optical fiber, $F_{j,i}$ represents the percentage of the $i^{th}$ volume element covered by the $j^{th}$ scintillating optical fiber, $\kappa_j$ represents the scintillation efficiency of the $j^{th}$ scintillating optical fiber (i.e. the number of scintillation photons emitted per unit of deposited dose), $\lambda$ accounts for the differential light attenuation along the $j^{th}$ scintillating optical fiber, $u_i$ represents the position on the scintillating optical fiber with respect to the reference point on the fiber and $D_{i,norm}$ represents the dose deposited in the $i^{th}$ volume element of the known normalization dose distribution (in vectorial form). It will be understood that equation (4) and (4a) represent an approximation that is normally valid only when the $\lambda_j$ term in equation (1), accounting for differential light attenuation along the scintillating optical fiber, is linear in u, and that under this approximation the projection calculated using equation (4) will be approximately independent of the light attenuation in the scintillating optical fiber.

Also provided herein are two exemplary methods of determination of the incident dose distribution on an array of scintillating optical fibers (e.g. the imaging planes 19, or 125) rotating around a pre-determined axis of rotation (e.g. central axis of rotations 15, 115 or 131). A first determination method uses iterative reconstruction techniques on the measured weighted dose line integrals in conjunction with a total variation (TV) minimization of the resultant dose pattern, with the total variation (TV) of the 2D dose distribution being defined as:

$$TV = \sum_i \sqrt{(D_i - D_{i-1})^2 + (D_i - D_{i-m})^2} \quad (5)$$

where $D_i$ represents the dose measured in the $i^{th}$ volume element 130 as shown in FIG. 8 and m is the number of such volume elements in each row of the 2D dose distribution.

The iterative reconstruction technique used in this first method of determination can be an algebraic reconstruction technique (ART). For example, suppose the incident dose distribution $\vec{D}$ (in vectorial form) can be described using:

$$p_j = B_j \cdot D \quad (6)$$

where $B_j$ represents the row of the modified projection matrix associated with $p_j$, which represents the $j^{th}$ weighted dose line integral of the incident dose distribution measured as described herein. Using this technique the $n^{th}$ iteration of the reconstructed dose distribution ($\vec{D}^{(n)}$) can be obtained from the previous iteration ($\vec{D}^{(n-1)}$) by the following formula:

$$\vec{D}^{(n)} = \vec{D}^{(n-1)} + \beta_n \cdot \frac{B_j}{\|B_j\|^2}\left(p_j - B_j \cdot \vec{D}^{(n-1)}\right) \quad (7)$$

where $\beta_n$ is the control parameter of the $n^{th}$ iteration, $B_j$ is the $j^{th}$ row of the projection matrix associated with $p_j$, the $j^{th}$ weighted dose line integral measured as described herein.

The iterative reconstruction technique used in this first method of determination can also be an expectation-maximization technique (EM). For example, the $n^{th}$ iteration of the reconstructed dose distribution ($\vec{D}^{(n)}$) can be obtained from the previous iteration ($\vec{D}^{(n-1)}$) by the following formula:

$$D_i^{(n)} = D_i^{(n-1)} \cdot \frac{1}{\sum_{j=1}^{N} b_{j,i}} \left( \sum_{j=1}^{N} b_{j,i} \frac{p_j}{B_j \cdot \vec{D}^{(n-1)}} \right) \quad (8)$$

where $D_i^{(n)}$ represents the dose measured in the $i^{th}$ volume element 130 in the $n^{th}$ iteration of the reconstructed dose distribution, $b_{j,i}$ is the element of the matrix B associated with the $i^{th}$ volume element and the $j^{th}$ weighted dose line integral measured as described herein, $B_j$ is the $j^{th}$ row of the projection matrix associated with $p_j$, the $j^{th}$ weighted dose line integral measured as described herein.

The total variation (TV) minimization technique using this first method of determination can be a steepest-descent method. For example, the total variation of the reconstructed dose distribution ($\vec{D}^{(n)}$) can be diminished by the following equation:

$$D_i^{(n')} = D_i^{(n)} - \alpha_n \frac{\partial TV}{\partial D_i^{(n)}} \quad (9)$$

where $D_i^{(n)}$ represents the dose measured in the i$^{th}$ volume element 130 in the n$^{th}$ iteration of the reconstructed dose pattern after TV minimization, $\alpha_n$ is the control parameter of the n$^{th}$ iteration of the TV minimization and TV is calculated using Equation 5.

The two control parameters $\alpha_n$ or $\beta_n$ (or both) can be adjusted so that the dose distribution modification caused by the iterative reconstruction technique is of the same magnitude as the dose pattern modification caused by the TV minimization. It will be understood that, by performing a plurality of iterations in the first determination method described above, the reconstructed dose pattern will tend to more closely approach the actual delivered dose pattern, under the assumption that the incident dose pattern has a low total variation.

A second determination method uses linear programming algorithms to determine the dose in each volume element 130 by linear optimization. For example and using the representations of Equations 6 and 6a, the optimization problem used in this determination method may include the following:

$$\text{Minimize} \quad \sum_j R_j \text{ subject to} \begin{cases} \vec{B}_j \cdot \vec{D} \leq (1+r)p_j & \forall\, p_j \\ \vec{B}_j \cdot \vec{D} \geq (1-r)p_j & \forall\, p_j \\ \vec{B}_j \cdot \vec{D} - R_j \leq p_j & \forall\, p_j \\ \vec{B}_j \cdot \vec{D} + R_j \geq p_j & \forall\, p_j \\ \text{Physical dose distribution constraints} \\ D_i \geq 0 \\ R_j \geq 0 \end{cases} \quad (10)$$

where $R_j$ is the j$^{th}$ element of the residual vector that represents the difference between the projection $\vec{B}_j \cdot \vec{D}$ calculated from the reconstructed incident dose distribution and the measured weighted dose line integral $p_j$, and r generally represents the maximum allowed difference between the projection $\vec{B}_j \cdot \vec{D}$ calculated from the reconstructed incident dose pattern and the measured weighted dose line integral $p_j$.

The physical dose distribution constraints generally ensure that the reconstructed dose pattern is physically acceptable. Such constraints can ensure that the dose distribution is smooth (i.e. not noisy) and/or that the dose gradient between two adjacent volume elements is inferior to a certain threshold. In some cases, such constraints can be represented mathematically for example by:

$$N(1 + h_{max}) \cdot D_i - \sum_{k=1}^{N} D_k \geq -\eta \quad (11)$$

$$N(1 - h_{max}) \cdot D_i - \sum_{k=1}^{N} D_k \leq \eta \quad (12)$$

where the indices k applies to the N neighboring volume elements of the i$^{th}$ volume element $D_i$, and $h_{max}$ and $\eta$ are constants regulating the physical dose distribution constraints. Such constants $h_{max}$ and $\eta$ can be adjusted based on a previous reconstruction of the dose pattern or a theoretical dose pattern, in order for the constraints to be more permissive in regions of high dose gradient and more severe in regions of dose plateau.

While certain features have been illustrated and described herein, many modifications, substitutions, changes, and equivalents will now occur to those of ordinary skill in the art. It is, therefore, to be understood that the appended claims are intended to cover all such modifications and changes.

The invention claimed is:

1. A dosimeter for use on a radiotherapy machine having a radiation source, the dosimeter comprising:
   a scintillation assembly configured to generate a light output in response to incident radiation distribution thereon from the radiation source; and
   at least one photo-detector operable to convert optical energy transmitted by the scintillation assembly to electrical signals for determining at least one of actual two-dimensional (2D) or actual three-dimensional (3D) dose distribution using tomographic reconstruction algorithms;
   wherein the scintillation assembly is composed of a plurality of scintillating optical fibers that are embedded in and span lengthwise across a phantom medium;
   wherein the scintillating optical fibers are made of a material that has been conditioned using UV light in order to increase their optical attenuation.

2. The dosimeter of claim 1, wherein the scintillating optical fibers have a length of a few centimeters or more.

3. The dosimeter of claim 1, wherein the phantom medium is made of a material with properties relative to radiation that are similar to the material used for the scintillating optical fibers.

4. The dosimeter of claim 1, wherein the scintillating optical fibers are made of a water-equivalent material.

5. The dosimeter of claim 1, wherein a plurality of collection optical fibers are coupled to at least one of the two opposing ends of the scintillating optical fibers and are adapted to transmit light output coming from one or both ends of each scintillating optical fiber to the at least one photo-detector.

6. The dosimeter of claim 1, wherein the scintillating optical fibers are disposed in at least one imaging plane.

7. The dosimeter of claim 6, wherein the at least one imaging plane is formed into at least one disk of a known radius.

8. The dosimeter of claim 6, wherein the at least one imaging plane is formed on the external surface of cylinders of known lengths and radii.

9. The dosimeter of claim 1 including a rotator having an axis of rotation orthogonal to a radiation beam axis, the rotator for rotating the photo-detector and the scintillating assembly about the axis of rotation.

10. The dosimeter of claim 1, wherein the scintillating assembly is made of water-equivalent material.

11. A dosimeter assembly including the dosimeter of claim 1 and a treatment table, wherein the scintillating assembly is located on the treatment table at or near a height of treatment delivery.

* * * * *